Nov. 24, 1970 H. C. SWIM ET AL Plant Pat. 3,007
ROSE PLANT
Filed Jan. 27, 1969
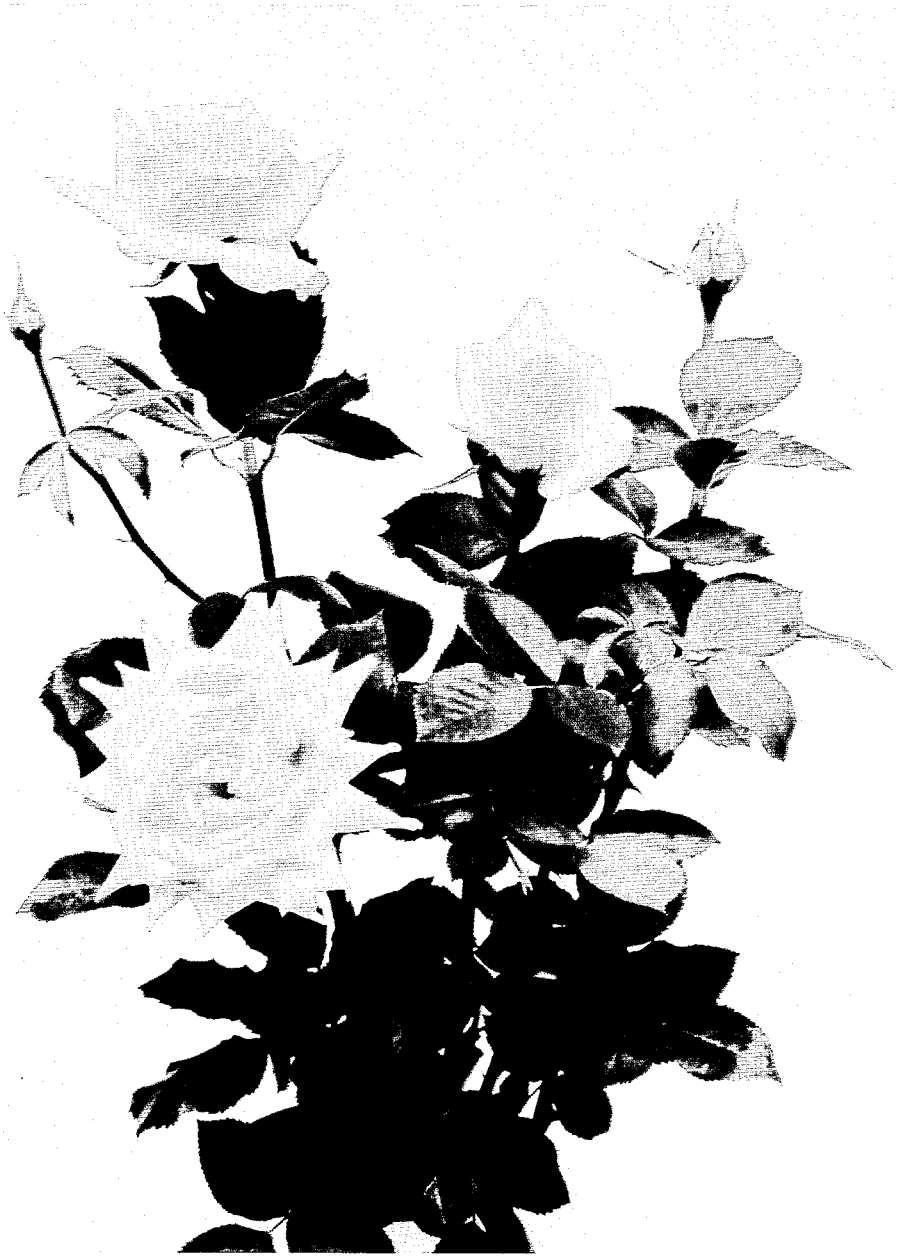
Inventors.
H. C. Swim
O. L. Weeks
By: Robb & Robb
Attorneys.

United States Patent Office

Plant Pat. 3,007
Patented Nov. 24, 1970

3,007
ROSE PLANT

Herbert C. Swim and O. L. Weeks, Ontario, Calif., assignors to O. L. Weeks, doing business as Weeks Wholesale Rose Grower, Ontario, Calif.

Filed Jan. 27, 1969, Ser. No. 794,427
Int. Cl. A01h 5/00
U.S. Cl. Plt.—17 1 Claim The present invention relates to a new and distinct variety (cultivar) of rose plant of the grandiflora class, which was originated by us by crossing the rose variety known as "Camelot" (Plant Pat. No. 2,371) with an unnamed and unpatented seedling of the rose variety known as "Montezuma" (Plant Pat. No. 1,383) × the rose variety known as "War Dance" (Plant Pat. No. 2,017).

As the result of this breeding, we have produced a new and improved rose variety which is distinguished from its parents, as well as from all other rose varieties of which we are aware, as evidenced by the following unique combination of characteristics which are outstanding in the new variety:

(1) A tall and bushy plant habit, with somewhat lax flower stems, particularly on the side blooms in the clusters;

(2) A very vigorous habit of growth, with moderately slender canes;

(3) Moderately thin but leathery leaves;

(4) Flowers of large size for the grandiflora class, with good petalage ranging from 60 to 80 petals;

(5) Substantially greater than average flower substance;

(6) A bright orange-red flower color;

(7) A substantially longer than average vase-life of the flowers;

(8) Better than average resistance to powdery mildew; and (9) A penetrating tea-rose flower fragrance.

In comparison with its seed parent "Camelot," the plants of the new variety are more spreading in habit and more thickly branched; the canes and stems are substantially more slender; the flower production, while intermittent or nearly so, is substantially more nearly continuous and the total number of flowers produced in a season is approximately fifty percent greater than is typical of "Camelot;" and the flowers of the new variety have substantially more petals, are more fragrant and have more of the orange and red colors.

As compared with its unnamed pollen parent, the plant of the new variety is tall in habit as distinguished from the relatively stumpy plant of only average height which is typical of this parent variety; its leaves are relatively thin instead of being quite thick and heavy like those of this parent; the canes are moderately light in caliper instead of being relatively short and heavy in caliper like those of this parent; the flowers have much greater petalage (from 60 to 80 petals as contrasted to approximately 30 petals in the parent flowers); and the flowers of the new variety are bright orange red in color, whereas those of this parent are deep brick-red, sometimes with a rusty overlay.

A sexual reproduction of our new variety by budding, as performed at Chino, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Md., except where general color terms of ordinary dictionary significance are obvious:

Type: Tall; bush; outdoor; seedling; for cut flowers and for garden decoration.
Class: Grandiflora.
Breeding: Seedling.
*Seed parent.*—"Camelot."
*Pollen parent.*—An unnamed seedling of "Montezuma" × "War Dance."
Propagation: Holds its distinguishing characteristics through succeeding propagations by budding.

FLOWER

Locality where grown and observed: Chino, Calif.
Flowers borne: Both singly and two, three or more to stem in irregular clusters; on central stems of normal strength but on weak side stems in the clusters.
Quantity of bloom: From free to abundant outdoors, but somewhat less free in greenhouse.
Continuity: From intermittent to nearly continuous.
Fragrance: Penetrating.
*Nature.*—Tea.
Bud:
*Peduncle.*—Medium length; medium caliper on central flower, but weak and bending on side blooms of clusters; smooth except for a few thin hairs. Color: Yellowish.
*Before calyx breaks.*—Size: From medium to large. Form: Medium length; pointed; with a conspicuous neck; with foliaceous appendages on the surface of the bud; sometimes with slender, much-cut foliaceous parts extending beyond the tip of the bud equal to its length, but usually not extending beyond the tip of the bud, and sometimes entire.
*As calyx breaks.*—Color: Between Strong Yellowish Pink, Plate 7.5 R 7/9 and Strong Reddish Orange, Plate 7.5 R 6/12 at frst, quickly becoming between Dark Reddish Orange, Plate 7.5 R 4/11 and Vivid Red, Plate 5 R 5/13 at tip, but paling to near Brilliant Greenish Yellow, Plate 10 Y 9/9 at base.
*As first petal opens.*—Size: Medium. Form: Long; from pointed to urn-shaped. Color: Outside—Between Strong Red, Plate 5 R 4/12 and Vivid Red, Plate 5 R 5/13, except for abrupt change to small area of Brilliant Greenish Yellow, Plate 7.5 Y 9/8 at base. Inside—Slightly deeper color than Vivid Red, Plate 5 R 5/13, except for small area at base of near Brilliant Greenish Yellow, Plate 7.5 Y 9/8.
*Opening.*—Opens up well; is not retarded from opening by cold, hot, wet, or dry weather.
Bloom:
*Size (when fully open).*—Large for class; from 4½ inches to 5 inches.
*Petalage.*—Very double (many petals, usually with no stamens showing); from 60 to 80 petals; arranged regularly.
*Form.*—Very full and high-centered at first and remaining so; petals being at first loosely rolled outward but later becoming tightly rolled outward at maturity.

Petals:

*Texture.*—Thick; leathery.

*Apearance.*—Inside: Pebbly or crepey. Outside: From pebbly to furrowed and leathery.

*Shape.*—Outside: Nearly round; entire. Intermediate: Broadly obovate, with apex entire. Inside: Obovate; cuneate; with apex having 2 or 3 notches and usually pointed because of tightly rolled margins.

*Color.*—Usually fairly uniform except for occasional vegetative streak or band along midrib on guard petals when such petals occur.

This description of a newly opened flower was made from a rose grown in a greenhouse during the month of May at Chino, Calif.

*Color.*—Outer petal: Outside surface—Near Vivid Red, Plate 5 R 5/13 near center of petal, but somewhat deeper at apex and paling toward base to near Brilliant Greenish Yellow, Plate 7.5 Y 9/8. Inside surface—basic color is near Vivid Red, Plate 5 R 5/13, with varying degrees of overlay of near Strong Reddish Orange, Plate 7.5 R 5/13, particularly on veins, with base of Brilliant Yellow Green, Plate 2.5 GY 9/8; sometimes outer petal may have a vegetative streak on inner surface along midrib varying in both width and length and sometimes being quite narrow and short, but at other times being as much as ⅛ inch wide and extending three-quarters of distance to apex; streak may also sometimes become laciniated at upper end. Intermediate petal: Outside surface—basic color is between Deep Yellowish Pink, Plate 5 R 6/11 and Vivid Red, Plate 5 R 5/13, but veins are marked quite faintly with Strong Red, Plate 2.5 R 5/12; base is Brilliant Greenish Yellow, Plate 7.5 Y 9/8. Inside surface—basic color is near Vivid Red, Plate 5 R 5/13, with varying degrees of overlay of Strong Reddish Orange, Plate 7.5 R 5/13, with small area at base Brilliant Yellow, Plate 2.5 Y 9/9. Inner petal: Outside surface—near Deep Yellowish Pink, Plate 5 R 6/11, with veins of Strong Red, Plate 2.5 R 5/12, and with base Brilliant Greenish Yellow, Plate 7.5 Y 9/8. Inside surface—between Strong Reddish Orange, Plate 7.5 R 6/12 and Strong Reddish Orange, Plate 7.5 R 5/13, except at base which is Brilliant Yellow, Plate 2.5 Y 9/9.

This description was made from a rose that was open for three days in a greenhouse during the month of May at Chino, Calif.

*Color.*—Outer petal: Outside surface—upper part of petals near Vivid Red, Plate 5 R 5/13, paling toward base to Strong, Yellowish Pink, Plate 5 R 7/9, and changing entirely at base to Brilliant Greenish Yellow, Plate 7.5 Y 9/8. Inside surface—deep Yellowish Pink, Plate 5 R 6/11, with some overlay of Strong Reddish Orange, Plate 7.5 R 6/12 on veins and midrib, and with base near Brilliant Greenish Yellow, Plate 7.5 Y 9/8. Inner petal: Outside surface—dominantly Deep Yellowish Pink, Plate 5 R 6/11, but shading toward Deep Pink, Plate 2.5 R 6/11 at apex progressing toward base dominantly Strong Yellowish Pink, Plate 10 R 7/9, and with base Brilliant Greenish Yellow, Plate 7.5 Y 9/8. Inside surface—dominantly between Deep Yellowish Pink, Plate 5 R 6/11 and Strong Reddish Orange, Plate 7.5 R 6/12, with base Brilliant Yellow, Plate 2.5 Y 9/9.

*General color effect.*—Newly opened flower: Between Vivid Red, Plate 5 R 5/13 and Strong Reddish Orange, Plate 7.5 R 5/13. 3-days open: Between Strong Red, Plate 2.5 R 5/12 and Vivid Red, Plate 5 R 5/13.

*Behavior.*—Drop off cleanly except for occasional petaloids.

*Flower longevity.*—On bush in garden: Substantially better than average. Cut roses grown in greenhouse and kept at living-room temperatures: 6 days in May.

REPRODUCTIVE ORGANS

Stamens: From few to medium number; arranged irregularly about pistils; mixed with petaloids.

Filaments: Short; few without anthers.

*Color.*—White.

Anthers: Small for class; open at various times.

*Color.*—White, except for valves.

Pollen: Sparse.

*Color.*—From yellowish to straw color.

Pistils: Few.

Styles: Uneven; long; thin caliper; loosely separated.

Stigma:

*Color.*—White or nearly so.

Ovaries: Some enclosed in, but most protruding from calyx.

Hips: Seldom sets hips; none observed.

Sepals: Permanent; long; recurved.

Seeds: Very few; large.

PLANT

Foliage:

*Leaves.*—Compound of 3 to 5 leaflets; normal abundance; medium size; thin; leathery.

*Leaflets.*—Shape: Ovoid. Apex: Acute. Base. From round to acute. Margin: Simply serrate.

*Color.*—Mature: Upper surface—dark green. Under surface—from normal to light grey-green. Young: Upper surface—light green, with bronze-red veins, midribs and margins. Under surface—light grey-green, with reddish purple dominating veins and midribs until leaves start to mature.

*Rachis (the supporting stem of the compound leaf).*—From light to medium weight. Upper side: Grooved, with ridges sparsely lined with small stipitate glands. Under side: Sparsely prickly.

*Stipules.*—Moderately short; moderately narrow; with moderately short points turning out at an angle of about 45°.

*Disease resistance.*—Substantially better than average resistance to powdery mildew when grown in greenhouse, as determined by comparison with other varieties grown under comparable conditions at Chino, Calif.

Growth:

*Habit.*—Tall; bushy; upright-spreading; much-branched.

*Growth.*—Very vigorous.

*Canes.*—Moderately light caliper.

*Main stems.*—Color: Dull green. Large prickles: Several; long, straight; with long, narrow base; color—grey-brown. Small prickles: Few; color—grey-brown. Hairs: None.

*Branches.*—Color: Dull green. Large prickles: Several; long; straight; with long, narrow base; color—brown. Small prickles: From none to few; color—brown. Hairs: None.

*New shoots.*—Color: Yellowish green bark. Large prickles: Several; long; straight; with long, narrow base; color—reddish purple, with light green points. Small prickles: None. Hairs: None.

I claim:

1. A new and distinct variety of rose plant of the grandiflora class, substantially as herein shown and described, characterized particularly as to novelty by the unique combination of a tall and bushy plant habit, with somewhat lax flower stems, particularly on the side blooms in the clusters, a very vigorous habit of growth, with moderately slender canes, moderately thin but leathery leaves, flowers of large size for the grandiflora class, with good petalage ranging from 60 to 80 petals, substantially greater than average flower substance, a bright orange-red flower color, a substantially longer than average vase-life of the flowers, better than average resistance to powdery mildew, and a penetrating tea-rose flower fragrance.

No references cited.

ROBERT E. BAGWILL, Primary Examiner